US010032269B2

(12) United States Patent
Lelong et al.

(10) Patent No.: US 10,032,269 B2
(45) Date of Patent: Jul. 24, 2018

(54) METHOD OF DETERMINING AN INDICATOR FOR THE STABILITY OF A BONE IMPLANT

(71) Applicant: Medimaps Group S.A., Plan-les-Ouates (CH)

(72) Inventors: Christophe Lelong, Bordeaux (FR); Renaud Winzenrieth, Pessac (FR); Franck Michelet, Pessac (FR)

( * ) Notice: Subject to any disclaimer, the term of this patent is extended or adjusted under 35 U.S.C. 154(b) by 0 days.

(21) Appl. No.: 14/775,903

(22) PCT Filed: Mar. 19, 2014

(86) PCT No.: PCT/IB2014/059963
§ 371 (c)(1),
(2) Date: Sep. 14, 2015

(87) PCT Pub. No.: WO2014/147566
PCT Pub. Date: Sep. 25, 2014

(65) Prior Publication Data
US 2016/0035089 A1 Feb. 4, 2016

(30) Foreign Application Priority Data

Mar. 19, 2013 (WO) .................. PCT/IB2013/052171

(51) Int. Cl.
*G06K 9/00* (2006.01)
*G06T 7/00* (2017.01)
(Continued)

(52) U.S. Cl.
CPC .............. *G06T 7/0012* (2013.01); *A61B 6/12* (2013.01); *A61B 6/14* (2013.01); *A61B 6/505* (2013.01);
(Continued)

(58) Field of Classification Search
CPC .. A61B 6/12; A61B 6/14; A61B 6/505; A61B 6/5217; A61C 19/04; A61C 8/0012;
(Continued)

(56) References Cited

U.S. PATENT DOCUMENTS 8,206,153 B2 * 6/2012 Suttin ...................... A61C 8/00
433/215
8,915,735 B1 * 12/2014 Carlsson .............. A61C 8/0022
433/174
(Continued)

FOREIGN PATENT DOCUMENTS

WO 2007009719 1/2007

OTHER PUBLICATIONS

"Bone Density at Implant Sites and its Relationship to Assessment of Bone Quality and Treatment Outcome" by Bergkvist G., Koh KJ, Sahlholm S., Klintstrom E, Lindh C.—in Int J Oral Maxillofac Implants. Mar.-Apr. 2010; 25(2): 321-8.
(Continued)

*Primary Examiner* — Tom Y Lu
(74) *Attorney, Agent, or Firm* — Sturm & Fix LLP

(57) ABSTRACT

A method of determining an indicator for the stability of a bone implant comprises providing a two- or three-dimensional image mage of a bone at a location where a bone implant is planned. Then determining a bone structural parameter, which is typically representative of trabecular bone texture at said location, from the two- or three-dimensional image, by a texture analysis of a two- or three-dimensional grey scale image in a region of interest at said location where the bone implant is planned. Finally, an indicator for the stability of the planned bone implant after implantation is determined from the bone structural parameter and from implant stability data.

10 Claims, 5 Drawing Sheets

(51) Int. Cl.
*A61B 6/12* (2006.01)
*A61B 6/14* (2006.01)
*A61B 6/00* (2006.01)
*A61C 19/04* (2006.01)
*G06K 9/52* (2006.01)
*A61C 8/00* (2006.01)
*G06K 9/46* (2006.01)

(52) U.S. Cl.
CPC ................ *A61C 19/04* (2013.01); *G06K 9/52* (2013.01); *A61B 6/5217* (2013.01); *A61C 8/0012* (2013.01); *G06K 2009/4666* (2013.01); *G06T 2200/04* (2013.01); *G06T 2207/30008* (2013.01)

(58) Field of Classification Search
CPC .............. G06K 2009/4666; G06K 9/52; G06T 2200/04; G06T 2207/30008; G06T 7/0012; C12Q 1/6837; C12Q 1/689; G01N 1/2273; G01N 2001/2217
See application file for complete search history.

(56) References Cited

U.S. PATENT DOCUMENTS

| | | | |
|---|---|---|---|
| 2007/0140534 A1 | 6/2007 | Pothuaud | |
| 2009/0162813 A1* | 6/2009 | Glor | A61C 1/084 433/196 |
| 2011/0112654 A1* | 5/2011 | Faldt | A61L 27/54 623/23.57 |

OTHER PUBLICATIONS

"A Clinical Study of Alveolar Bone Quality Using the Fractal Dimension and the Implant Stability Quotient" by Dae-Hyun Lee et al in Journal of Periodontal Implant Science 2010; 40; 19-24—doi: 10.5051/jpis 2010.

International Search Report and Written Opinion for PCT/IB2014/059963.

* cited by examiner

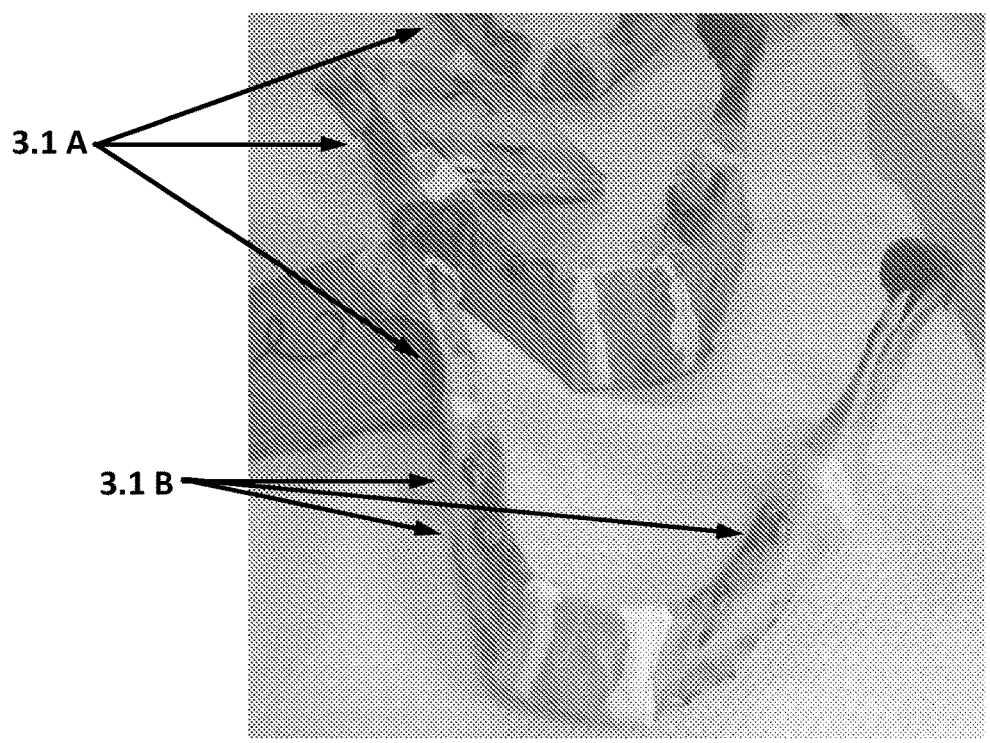
Figure 3.1
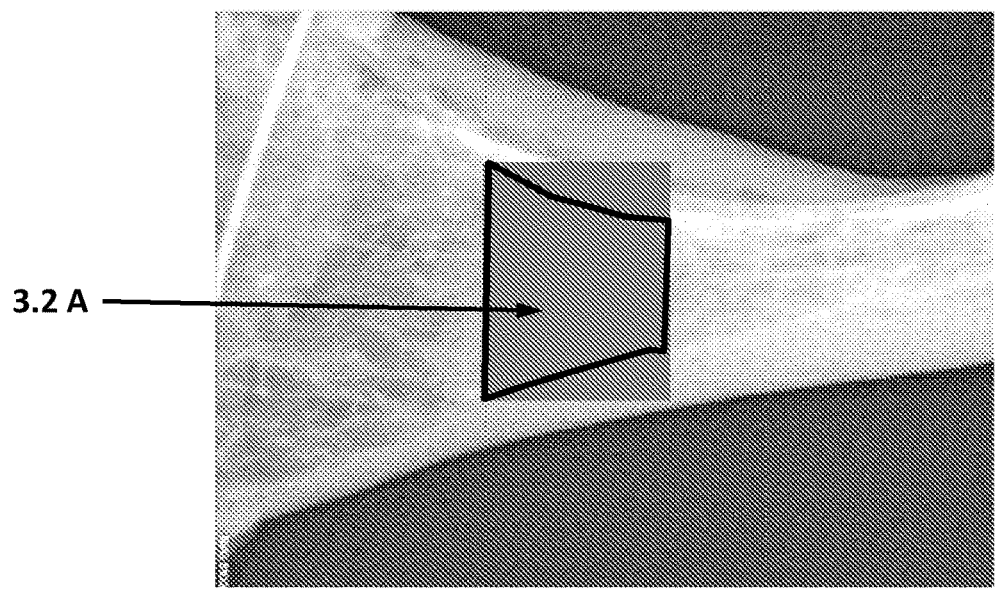
Figure 3.2

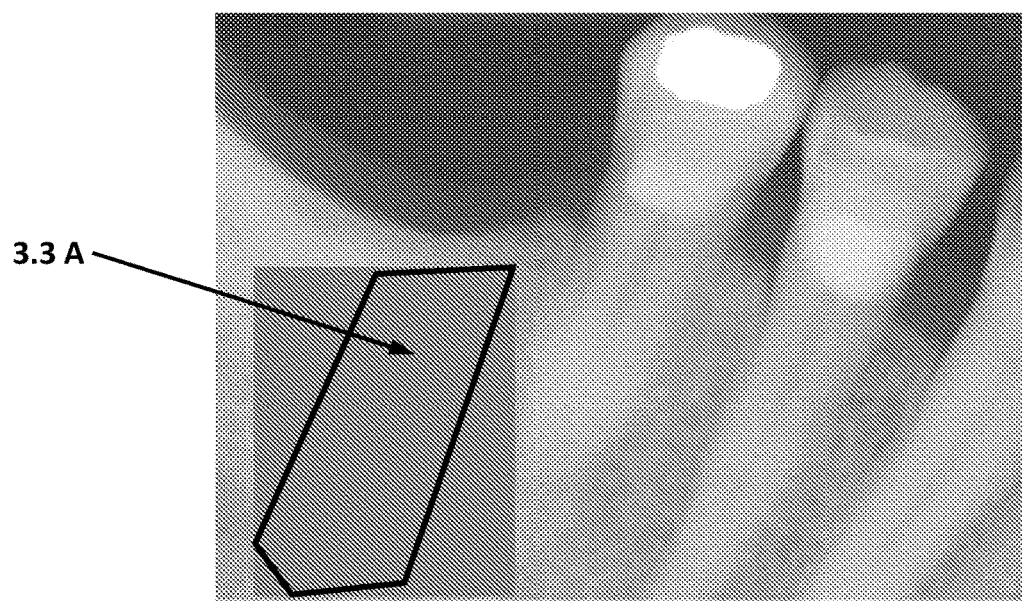
Figure 3.3
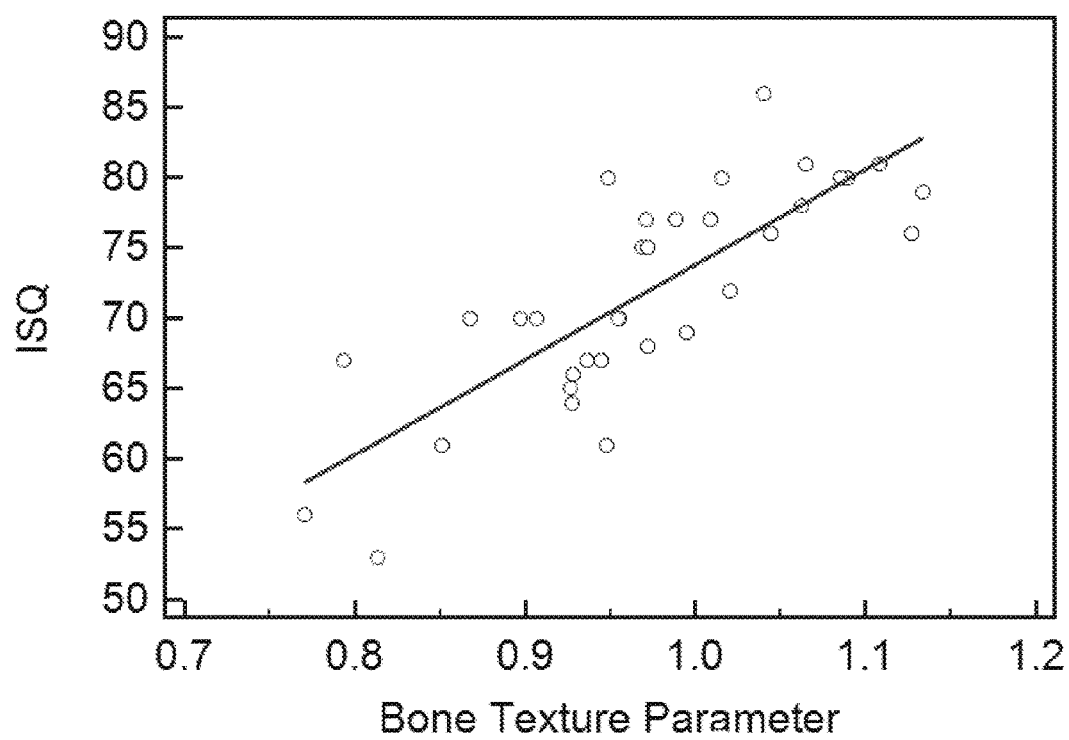
Figure 3.4

Table 1

|  | ISQ | Bone Texture Parameter | | | | | |
|---|---|---|---|---|---|---|---|
|  |  | $C_1$ | $C_2$ | $C_3$ | $C_4$ | $C_5$ | $C_6$ |
| Implant 1 | 53 | 0,8131679 | 0,8007593 | 0,7537945 | 0,730382 | 0,730382 | 0,6946616 |
| Implant 2 | 65 | 0,9263149 | 0,8876526 | 0,8047708 | 0,7528099 | 0,7528099 | 0,648366 |
| Implant 3 | 72 | 1,020225 | 0,9790948 | 0,8948537 | 0,8417435 | 0,8417435 | 0,7446525 |
| Implant 4 | 61 | 0,9481223 | 0,9360681 | 0,8827842 | 0,8558148 | 0,8558148 | 0,8193648 |
| Implant 5 | 66 | 0,9435596 | 0,9282058 | 0,8632507 | 0,8230532 | 0,8230532 | 0,7573321 |
| Implant 6 | 64 | 0,9275156 | 0,8986505 | 0,8259727 | 0,7847546 | 0,7847546 | 0,7192265 |
| Implant 7 | 67 | 0,9444891 | 0,9277357 | 0,8819591 | 0,857947 | 0,857947 | 0,8106248 |
| Implant 8 | 70 | 0,8672432 | 0,855437 | 0,8067641 | 0,7803822 | 0,7803822 | 0,7303858 |
| Implant 9 | 67 | 0,7933151 | 0,7784995 | 0,7315495 | 0,7075922 | 0,7075922 | 0,663307 |
| Implant 10 | 70 | 0,9551411 | 0,9231372 | 0,8571209 | 0,822606 | 0,822606 | 0,7598301 |
| Implant 11 | 81 | 1,064255 | 1,016993 | 0,9291897 | 0,8756976 | 0,8756976 | 0,7786801 |
| Implant 12 | 70 | 0,9543406 | 0,9094934 | 0,824386 | 0,7731435 | 0,7731435 | 0,6838735 |
| Implant 13 | 70 | 0,9071115 | 0,8804689 | 0,8151505 | 0,7783229 | 0,7783229 | 0,7069087 |
| Implant 14 | 80 | 1,014886 | 0,9901293 | 0,9226469 | 0,8813239 | 0,8813239 | 0,801389 |
| Implant 15 | 77 | 1,008835 | 0,9879305 | 0,9241346 | 0,8833278 | 0,8833278 | 0,8020775 |
| Implant 16 | 77 | 0,9885809 | 0,953769 | 0,8760374 | 0,8256879 | 0,8256879 | 0,731109 |
| Implant 17 | 80 | 0,9491522 | 0,9210959 | 0,8490548 | 0,8050475 | 0,8050475 | 0,7210377 |
| Implant 18 | 75 | 0,9714611 | 0,9714529 | 0,9349592 | 0,9169115 | 0,9169115 | 0,8992974 |
| Implant 19 | 70 | 0,897253 | 0,9013855 | 0,8657495 | 0,8498332 | 0,8498332 | 0,8252636 |
| Implant 20 | 61 | 0,8511326 | 0,8567288 | 0,8254833 | 0,8115602 | 0,8115602 | 0,7830774 |
| Implant 21 | 69 | 0,9949028 | 0,9708173 | 0,9114523 | 0,878977 | 0,878977 | 0,8224402 |
| Implant 22 | 68 | 0,9718147 | 0,9578782 | 0,9134892 | 0,8909948 | 0,8909948 | 0,8447514 |
| Implant 23 | 78 | 1,062375 | 1,017646 | 0,9211067 | 0,8588367 | 0,8588367 | 0,7397063 |
| Implant 24 | 76 | 1,126697 | 1,087827 | 0,9923978 | 0,9275284 | 0,9275284 | 0,8073369 |
| Implant 25 | 76 | 1,044182 | 0,9997502 | 0,9008185 | 0,8348384 | 0,8348384 | 0,7100292 |
| Implant 26 | 80 | 1,085286 | 1,042331 | 0,9461021 | 0,8794831 | 0,8794831 | 0,7548863 |
| Implant 27 | 75 | 0,9687048 | 0,9381366 | 0,8589485 | 0,8068632 | 0,8068632 | 0,7088504 |
| Implant 28 | 56 | 0,7709978 | 0,7597057 | 0,7091116 | 0,6833411 | 0,6833411 | 0,6402 |
| Implant 29 | 79 | 1,133743 | 1,094175 | 1,001237 | 0,9388073 | 0,9388073 | 0,8166186 |
| Implant 30 | 80 | 1,08953 | 1,080539 | 1,029729 | 0,9919749 | 0,9919749 | 0,9053497 |
| Implant 31 | 86 | 1,040287 | 1,008076 | 0,9255251 | 0,8702242 | 0,8702242 | 0,7704334 |
| Implant 32 | 77 | 0,971143 | 0,9566054 | 0,9056582 | 0,875442 | 0,875442 | 0,8207143 |
| Implant 33 | 81 | 1,108402 | 1,103363 | 1,055605 | 1,020889 | 1,020889 | 0,9371215 |
| Implant 34 | 67 | 0,9360821 | 0,894818 | 0,812473 | 0,7646346 | 0,7646346 | 0,6799996 |

Figure 3.5

Table 2

| | | Bone Texture Parameter | | | | | |
|---|---|---|---|---|---|---|---|
| | | $C_1$ | $C_2$ | $C_3$ | $C_4$ | $C_5$ | $C_6$ |
| ISQ | Correlation Coefficient | 0,794 | 0,786 | 0,740 | 0,666 | 0,666 | 0,417 |
| | Significance Level $p$ | <0.0001 | <0.0001 | <0.0001 | <0.0001 | <0.0001 | 0,0142 |
| | Number of implants $n$ | 34 | 34 | 34 | 34 | 34 | 34 |

Figure 3.6

METHOD OF DETERMINING AN INDICATOR FOR THE STABILITY OF A BONE IMPLANT

FIELD OF THE INVENTION

This invention relates to bone implantation and is particularly concerned with a method of determining an indicator for the stability of a bone implant.

BACKGROUND OF THE INVENTION

Numerous bone sites are used as acceptor sites for implant grafting and loading. In dentistry, these sites consist mainly in the mandible and upper or lower maxilla. In orthopaedics, mainly extremities of the femur (thigh bone), humerus or tibia (shinbone) are considered. These bones are composed of two osseous tissues: The dense cortical bone forms the hard outer layer of bone organs. The cancellous bone, or trabecular bone or spongy bone, has a higher surface area but is less dense, softer, weaker, and less stiff. It typically occurs at the ends of long bones, proximal to joints. Its primary anatomical and functional unit is the trabecula. The capacity of these bones to successfully accept an implant depends not only on patient characteristics, surgical technique and implant design but also on bone quality and density and on the structural organization and microstructures of the spongy bone moiety. Chances of satisfactory rehabilitation are based on initial stability of the implant loading as well as on the good biological and biomechanical osseointegration capacity of the implant.

Implant stability is achieved at two levels: the primary stability, which is the mechanical stability obtained immediately after implantation and the secondary stability which is obtained along the osseointegration process. Secure primary stability is both a good indicator and a prerequisite of secondary stability. Being able to assess with accuracy this primary stability as well as the secondary stability enables to design an appropriate surgery protocol and its follow-up.

A major challenge is to develop methodological tools that enable to understand the key elements which contribute to implant performance, in particular regarding implant primary stability.

Primary implant stability refers to the stability of an implant e.g. a dental implant immediately after implantation. Its value is derived from a mechanical engraving typically of a titanium screw implant in the patient's bone tissue. High initial stabilization may be an indication for immediate loading with prosthetic reconstruction.

The value of primary implant stabilization decreases gradually with reconstruction of bone tissue around the implant in the first weeks after surgery, ceding to secondary stability. Its character is quite different from the initial stabilization, because it results from the ongoing process of osseointegration. When the healing process is complete, the initial mechanical stability is fully replaced by biological stability. The most dangerous moment for implantation success is the moment of the lowest initial stabilization, pending sufficient bone reconstruction supporting long-term maintenance of the implant. Usually this occurs during the 3-4 weeks after implantation. If primary stability was not high enough following implantation, the implant's mobility is high and can cause failure.

Resonance frequency analysis (RFA—using the Osstell™ device) and the damping capacity assessment (Periotest™ technique) are the nondestructive intraoral testing methods for assessing implant stability after implantation. In the initial Periotest technology, an electronically controlled rod typically taps the implant a few times per second at a constant speed. The rod is decelerated when it enters in contact with the implant and its frequency is modified. When implants are stable, the deceleration is higher, and so is the damping effect of the tissues surrounding the implant. After hitting the implant, the rod recoils. A faster recoil indicates higher damping. The Periotest™ technology is intended to provide objective implant stability values used for evaluating implant-bone interface stability. Resonance frequency analysis (RFA) is a noninvasive and non-destructive quantitative measurement of implant integration by assessing changes in implant stability over time. This technology consists in the use of an adapter placed on a screw which is attached to the implant. Then a probe emits magnetic pulses at different frequencies that trigger the screw to vibrate. The adapter starts to vibrate, the probe listens to the tone and translates it into the resonance frequency (RF) to which corresponds an ISQ (Implant Stability Quotient) value. The higher the frequency, the more stable the implant is. ISQ is used as a scale that indicates the level of stability and osseointegration in dental implants. The ISQ scale typically ranges from 1 to 100, with the acceptable stability between 55-85 ISQ. In its most recent wireless version, RFA makes use of a magnetic peg—the so-called Smartpeg—attached to an implant or abutment. The peg is excited and the RF is expressed electromagnetically as ISQ units.

Although Periotest and RFA technologies have shown great promise in dentistry and have helped in adapting and improving implant technologies, they suffer from some drawbacks. The exact correlation of RFA values with bone density or cortical thickness have yet to be clearly established. Periotest technology shows inter-operator and inter-instrument variability. None of these technologies use or provide images of the acceptor site. Most importantly, both technologies allow an assessment of implant stability only after implant insertion or loading, thus limiting post-operative adaptations in the case of improper stability and causing patient discomfort by extended surgery times on implanted bones. They allow a surgeon to check implant integration but do not provide effective and reliable data to predict stability of a planned implant. No such opportunities are available to orthopaedics surgeons.

Implantology professionals use empirical protocols and mean values arising from their own expertise in their practice to design ad hoc implants and implanting surgery protocols. These values fit most surgical situations but do not allow dedicated solutions to out-of-range patients and clinical situations where implants suffer high risk of failure or can cause severe pain, leading to necessary complicated, and most often palliative, surgical interventions. Instead, objective and accurate measurement of predicted implant stability would allow surgeons to make well-informed decisions about implant protocol choices on a case-by-case basis, so that patients could enjoy the benefits of the personalized protocols with higher chances of success.

An Article "Bone density at implant sites and its relationship to assessment of bone quality and treatment outcome" by Bergkvist G, Koh K J, Sahlholm S, Klintström E, Lindh C. in Int J Oral Maxillofac Implants. 2010 March-April; 25(2):321-8 investigates the relationship between bone mineral density (BMD) before implant placement, implant stability measures at implant placement, and marginal bone loss of immediately loaded implants after 1 year in situ. The method uses computed tomographic examination as a preoperative method to assess jawbone density before implant placement. However, after 1 year there were no differences in survival rates or changes in marginal bone density between implants placed in bone tissue of different density. This can be explained in that bone mass or density is not a useful parameter for determining implant stability.

An article ("the JPIS Article") entitled "A clinical study of alveolar bone quality using the fractal dimension and the implant stability quotient" by Dae-Hyun Lee et al in Journal of Periodontal Implant Science 2010; 40; 19-24—doi: 10.5051/jpis.2010 discusses the evaluation of dental implant stability using fractal analysis to assess bone density. The purpose of this study is to investigate whether the fractal dimension from a panoramic radiograph is related to the primary stability of the implant as represented by RFA. The authors found a linear correlation that was statistically significant between the fractal dimension computed from panoramic X-ray images and ISQ values of RFA. They conclude that the fractal dimension of bone may be a useful method for indicating a general pre-surgical treatment plan. However, The cited JPIS article is limited to panoramic X-ray images in which the fractal dimension is computed and compared to the Implant Stability Quotient (RFA). The fractal dimension is intended to be a predictor of the sole primary stability. Panoramic X-ray images are however known to be very distorted images and thus not effective for measuring a parameter like the fractal dimension which would be relevant only on images exhibiting scale-invariant spatial properties; a panoramic image cannot have any scale invariant spatial property.

SUMMARY OF THE INVENTION

According to its main aspect the invention provides a method of determining an indicator for the stability of a bone implant, the method comprising the steps of: Providing a two- or three-dimensional image of a bone at a location where a bone implant is planned; Determining a bone structural parameter at said location from the two- or three-dimensional image; Providing implant stability data which is related to data representing the bone structural parameter, and Determining, from the determined bone structural parameter and from said implant stability data, an indicator for the stability of the planned bone implant after implantation at said location.

The invention applies to any kind of 2D or 3D X-ray scan, except panoramic images because the level of distortion that appears in a panoramic image prevents it from being used.

The bone implant can be selected from the group consisting of a dental implant and an orthopaedic implant. Moreover, the bone implant can comprise a biomaterial, such as a bone substitute and in this case the invention provides a method for determining an indicator of its osseointegration. In many cases, the bone implant comprises a screw of inert material in particular of titanium.

The method can include determining said indicator of the stability of a bone implant as a primary stability, which is the stability of the implant at the day of implanting the implant into the bone and/or determining said indicator of the stability of a bone implant as a secondary stability, which is the stability of the implant after healing and/or after osseointegration of the implant.

Thus, unlike the aforesaid JPIS Article which is suitable only for assessing primary stability, the method according to the invention is suitable for predicting both primary and secondary stability.

When a three-dimensional image is provided of the bone at the location where a bone implant is planned, the three-dimensional image is either projected onto a plane to be processed as a two-dimensional image for determining the bone structural parameter or is processed as a three-dimensional image for determining the bone structural parameter.

In the method, the implant stability data can be evaluated by Resonance Frequency Analysis of reference implants or by assessing the damping capacity of a reference implant. The stability of the implant can also be evaluated e.g. by Resonance Frequency Analysis either immediately after implantation or after the osseointegration period.

The bone structure/texture parameter used in the invention is not a measurement of the fractal dimension, and cannot be compared to the fractal dimension in such type of image; it is computed from the experimental variogram of the grey levels in the image. In the JPIS article, the fractal dimension is performed using a tile-counting method from a skeletonized image which is very different from the experimental variogram measurement performed from an image containing a trabecular bone texture used in invention.

In the present invention, the bone texture parameter is computed directly on the grey levels contained in the X-ray image, and the local variations in the pixels intensities decide mostly on value of the final estimator; conversely, in the cited JPIS article, the fractal dimension is computed from skeletonized binary images, where no information remains on the local contrasts.

Both the cited invention and the cited JPIS article refer to RFA since it is the gold standard to evaluate the stability of an object inserted into a material. Nevertheless, in the cited article, the RFA is only used as a comparison while in the present invention, the RFA values are incorporated in the process, being used to define the optimal configuration of the bone texture parameter.

The invention provides an estimate of the implant primary or secondary stability while the cited article is only focused on the primary stability.

The cited JPIS article exhibits correlations between RFA and the fractal dimension which are whether very low or even not significant showing that the method described is not suitable to obtain a robust predictor of the implant primary stability.

In one embodiment, evaluation of the implant data comprises biomechanical testing such as measuring the pull-out strength of an implant.

In another embodiment, evaluation of the implant data comprises a biological analysis of the implant's osseointegration.

Another aspect of the invention involves evaluating the bone structural parameter prior to surgery as a predictor of implant integration and after surgery to monitor implant integration.

The aforementioned bone structural parameter is typically representative of trabecular bone texture.

The bone structural parameter is advantageously determined by a texture analysis of a two- or three-dimensional grey scale image in a region of interest at said location where the bone implant is planned.

In a preferred embodiment, the bone structural parameter is determined by a series of the following steps performed by a computational device configured to process a digitized two- or three-dimensional image: a) retrieving a grey level $h(O)$ for each pixel in a region of interest of the two-dimensional image; b) selecting a representative set of pixels at a distance r around $h(O)$; c) retrieving the grey level $h(r)$ of said set of pixels; d) computing a variance V(r) of the grey levels with the formula:

$$V(r)=[h(r)-h(O)]^2;$$

e) tracing a curve associated with V(r) on a log-log scale; and f) determining the slope of the curve as said bone structural parameter.

BRIEF DESCRIPTION OF DRAWINGS

The invention will further be described by way of example with reference to the accompanying drawings, in which:

FIG. 3.1 is a view of some reference bone samples after implants were placed.

FIG. 3.2 is an X-ray image of a bone sample, overlaid by a drawn region of interest at the location where an implant will be placed.

FIG. 3.3 is an X-ray image of a patient's mandible, overlaid by a drawn region of interest at the location where an implant will be placed.

FIG. 3.4 is a graph of the maximal correlation between the Implant Stability Quotient and the Bone Texture Parameter.

FIG. 3.5 is a table, Table 1, showing for each implant (or the corresponding region of interest on the jaw bone) the value computed for the Bone Texture Parameter for each configuration and the ISQ.

FIG. 3.6 is a table, Table 2, exhibiting the correlation coefficients between the Bone Texture Parameter and the ISQ for each configuration.

DETAILED DESCRIPTION OF EMBODIMENTS OF THE INVENTION

Figure 1:
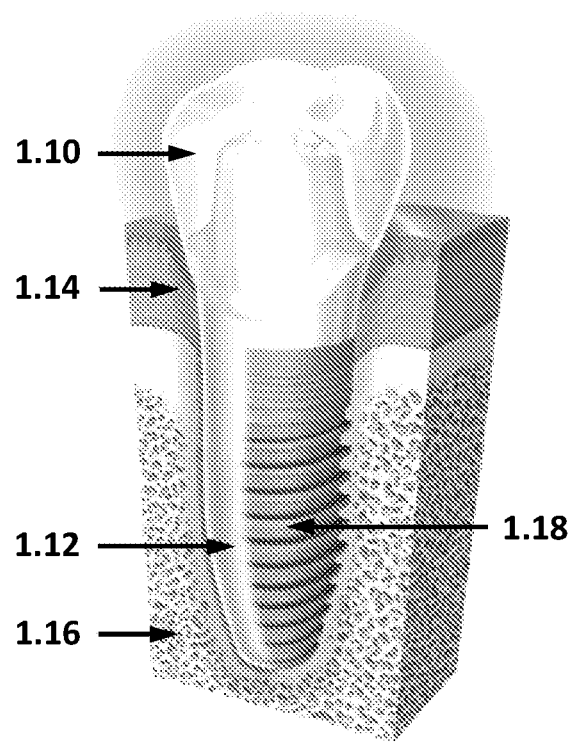
FIG. 1 is a cut-away view of a dental implant inserted into a jaw bone.

The present invention relates to a method to determine an indicator for the quality of a bone site intended to receive an implant, and that is used as a predictor for the stability of implants that will be screwed or glued to it. The preferred embodiment of this method is characterized by the use of imaging technology of the acceptor bone site that can make use of the quantitative analysis of spatial variability of grey levels in the scan image of the acceptor bone site prior to implant loading and screwing/gluing. Using dedicated software, the spatial variability of these shades of grey can be directly correlated to bone texture, which is a strong predictor of implant osseointegration. The output of the analysis methodology consists in a variogram representation of the digitalized optical measurements of the shades of grey within the image, so that the stability indicator for a given acceptor bone area is assessed by the mean value of the indicators for this area. For each pixel of the acceptor site image, the variability of surrounding pixels can be calculated as the sum of the square differences of their shade of grey intensity at a given distance of the reference pixel. These variations are then plotted using a log-log scale. Using a one-to-one mathematical function, the pixel area that can be computerized is defined and the indicator of stability is calculated as the slope of this function.

Imaging technology

Firstly, a two- or three-dimensional image is provided of a bone at a location where an implant is planned.

Images mentioned here are produced for example using X-ray imaging technologies, in particular digital X-ray radiography, two-photon absorption imaging, standard scanners and cone-beam scanners.

As mentioned, when a three-dimensional image is provided of the bone at the location where a bone implant is planned, the three-dimensional image is either projected onto a plane to be processed as a two-dimensional image for determining the bone structural parameter or is processed as a three-dimensional image for determining the bone structural parameter.

Providing two- or three-dimensional X-ray images of bones for the purpose of bone structure prognosis is for example described in US patent publications US2008/0031412 A1, US1010/09998212 A1 and US 2011/0036360 A1.

Digital X-ray imaging uses direct or indirect techniques: Both techniques can be used in numerical X-ray imaging.

Bone Structural Parameter

According to the inventive method, a bone structural parameter at said location where an implant is planned is derived from the two- or three-dimensional image. The bone structural parameter is for example representative of trabecular bone texture. The bone structural parameter can for example be determined by a texture analysis of a two- or three-dimensional grey scale image of the two-dimensional image in a region of interest at said location where the bone implant is planned.

Shades of grey are defined as luminance steps that differ by a defined amount within an image. The minimum difference between two shades of grey corresponds to the quantification step of the image. Contrast ratio is defined as being the maximum luminance value divided by the minimum luminance value, with the dynamic range being the number of shades of grey between minimum and maximum.

A preferred method of deriving the bone structural parameter is described in U.S. Pat. No. 7,609,867, summarised as the following steps performed by a computational device configured to process a digitized two- or three-dimensional image:

a) retrieving a grey level h(O) for each pixel in a region of interest of the two- or three-dimensional image;
b) selecting a representative set of pixels at a distance r around h(O);
c) retrieving the grey level h(r) of said set of pixels;
d) computing a variance V(r) of the grey levels with the formula:

$$V(r)=[h(r)-h(O)]^2;$$

e) tracing a curve associated with V(r) on a log-log scale; and
f) determining the slope of the curve as said bone structural parameter.

In the steps a) to f), a number of technical choices can be made for the computation and will change the value of the bone structural parameter. Part of our inventive method consists in adjusting these choices in order to maximize the correlation between the bone structural parameter and the implant stability.

Another method of deriving the bone structural parameter, described in FR2960762 A1, is based on selecting a region of interest area on a grey level image of a bone tissue, calculating the grey level and comparing this with a threshold limit. A value of an emission parameter is determined according to the value of the grey levels and the threshold. An image is acquired using an imaging apparatus provided with a new value of the emission parameter.

Implant Stability Data

The inventive method comprises providing implant stability data which is related to data representing the bone structural parameter.

The implant stability data is collected using bone samples (ex-vivo, from human cadavers or in-vivo, from patients' bones) and a set of reference implants; reference implants are implanted in said bone samples and the implants stability is evaluated using an implant stability meter which calculates the RFA of all implanted implants. The implant's stability is recorded immediately after implantation (primary stability) and/or after the osseointegration period (secondary stability, for in-vivo bones only).

Two- or three-dimensional images of said bone samples are acquired and the bone structural parameter is computed from said images, with various variables.

The implant stability data is used to select the appropriate variables. The selected variables are those who maximize the correlation between the bone structural parameter and the RFA. Several sets of variables are defined: one using the primary stability data to optimize the bone structural parameter as an indicator of the implant primary stability; another using the secondary stability data to optimize the bone structural parameter as an indicator of the implant secondary stability. Additional sets of variables may be used to optimize the bone structural parameter as an indicator of the implant stability in different bone types: mandible, maxillary, hip, femur, knee, tibia, shoulder, etc. Additional sets of variables may be used to optimize the bone structural parameter as an indicator of the implant stability of different types of implants: dental implants with various forms; orthopedic implants that may be pins, rods, screws or plates; bone substitutes (in this case, the bone structural parameter is an indicator of the implant osseointegration).

Determining the Indicator for Stability of the Planned Bone Implant

The inventive method provides for determining, from the determined bone structural parameter and from said implant stability data, an indicator for the stability of the planned bone implant after implantation at said location.

A two- or three-dimensional image of the bone intended to receive one or more implants is acquired. The bone structural parameter is computed from said image using the variables optimized for the determination of the primary stability (conversely of the secondary stability).

EXAMPLE 1

Dental Implant

FIG. 1 shows by way of example a cut-away view of a dental implant 18 inserted into a jaw bone 1.16. The jaw bone 1.16 is made of cortical bone and of trabecular bone. The quality of the trabecular bone is a key determinant of a good osseointegration of the implant. As shown, the tooth has a crown 1.10 above a tooth root 1.12 that passes through the gum 1.14 and extends down into the jaw bone 1.16. The tooth incorporates an implant 1.18 in the form of a screw made of inert material, preferably titanium.

Before the implant is fitted, an X-ray image is taken of the region of the jaw bone where the implant 1.18 is planned. This X-ray image is analyzed to determine a bone structural parameter representing trabecular bone texture, by a texture analysis of a two-or-three-dimensional grey level image in a region of interest at said location where the bone implant is planned. The bone structural parameter is designed to assess the quality of the trabecular bone. Preferably this analysis is performed using the above mentioned method described in U.S. Pat. No. 7,609,867. This bone structural parameter is compared with a set of predetermined values from a set of reference implants, as described above under "Implant Stability Data", using also selected variables from comparable bone types, namely mandible or maxillary.

The resulting calculation leads to values predicting whether the planned implant will be stable for its primary and secondary stability. If the results show that the implant should be stable, the dental surgeon can carry out the implant and shorten the delay before loading. If the result shows that the planned implant would be unstable, the dental surgeon can take any necessary measures.

After implantation, the primary and secondary stability can be checked by RFA measurements and compared with the predicted values.

EXAMPLE 2

Orthopaedic Implant

Figure 2:
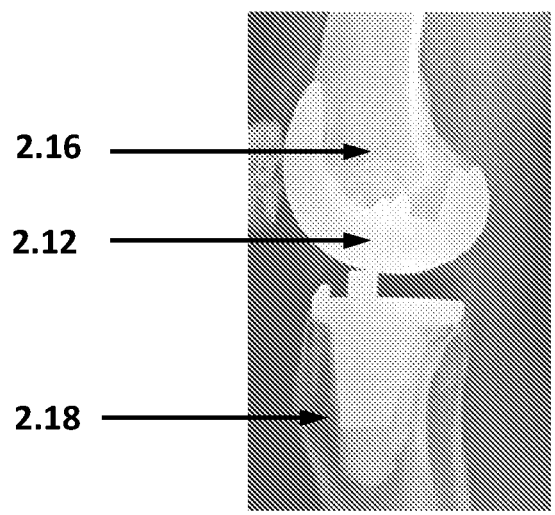
FIG. 2 is a cut-away view of an orthopedic implant inserted in a knee bone.

FIG. 2 shows by way of example an X-ray view of an orthopedic knee implant 2.12 inserted into a femur (thigh bone) 2.16 and a tibia (shin bone) 2.18. The femur 2.16 and the tibia 2.18 are made of cortical bone and of trabecular bone. The quality of the trabecular bone is a key determinant of a good osseointegration of the implant. As shown, the implant is inserted into femur and tibia bones, mainly in their trabecular part since it is the bone-to-implant contact surface in the trabecular bone (the bone that has the higher remodeling rate) that is a key determinant of a good osseointegration.

Before the implant is fitted, an X-ray image is taken of the region of the knee where the implant 2.12 is planned. This X-ray image is analyzed to determine a bone structural parameter representing trabecular bone texture, by a texture analysis of a two-or-three-dimensional grey level image in a region of interest at said location where the bone implant is planned. The bone structural parameter is designed to assess the quality of the trabecular bone. Preferably this analysis is performed using the above mentioned method described in U.S. Pat. No. 7,609,867. This bone structural parameter is compared with a set of predetermined value from a set of reference implants, as described above under "Implant Stability Data", using also selected variables from comparable bone types, namely knee.

The resulting calculation leads to values predicting whether the planned implant will be stable for its primary and secondary stability. If the results show that the implant should be stable, the orthopedic surgeon can carry out the implant and shorten the delay before restoring the function. If the result shows that the planned implant would be unstable, the orthopedic surgeon can take any necessary measures.

EXAMPLE 3

Primary Stability of a Dental Implant in the Posterior Mandible

Using a set of edentulous bone samples 3.1A (FIG. 3.1), namely mandibles, locations are defined where implants will be placed, namely in the posterior mandible. Images of the bone samples are taken, for example periapical X-ray images using standard imaging protocols (FIG. 3.2). For each resulting image, one or several regions of interest 3.2A are drawn over the bone where the implant is to be placed (FIG. 3.2). Then the texture analysis are performed, preferably using the above mentioned method described in U.S. Pat. No. 7,609,867. For each region of interest, the bone structural parameter is computed using several configurations $C_i$ (Table 1, FIG. 3.5).

Using the same set of bone samples, the reference dental implants are placed in the previously defined locations 3.1B (FIG. 3.1). The implants' stability is measured using reference frequency analysis with an Osstell device and the Implants Stability Quotients (ISQ) are determined (Table 2, FIG. 3.5).

For each region of interest and each configuration of the texture analysis, the correlation between the ISQ and the bone structural parameter is determined (Table 2, FIG. 3.6).

Last, the maximum of the correlation $C_l$ is determined (Table 2, FIG. 3.6) and the corresponding configuration of the texture analysis is stored. This correlation $C_l$ is specific for the evaluation of the primary stability of dental implants in the posterior mandible using this type of medical imaging device.

Using an X-ray image of a patient bone where an implant is planned (FIG. 3.3), namely posterior mandible, a region of interest 3.3A is drawn on the bone image where the implant is to be placed. The texture analysis is computed using the configuration $C_l$. The resulting value allows to predict whether the planned implant will be stable immediately after placement (primary stability). If the results show that the implant should be stable, the dental surgeon can carry out the implant and, for example, shorten the delay before loading. If the result shows that the planned implant would be unstable, the dental surgeon can take any necessary measures.

EXAMPLE 4

Primary stability of an Orthopaedic Implant in the Spine

Figure 4:
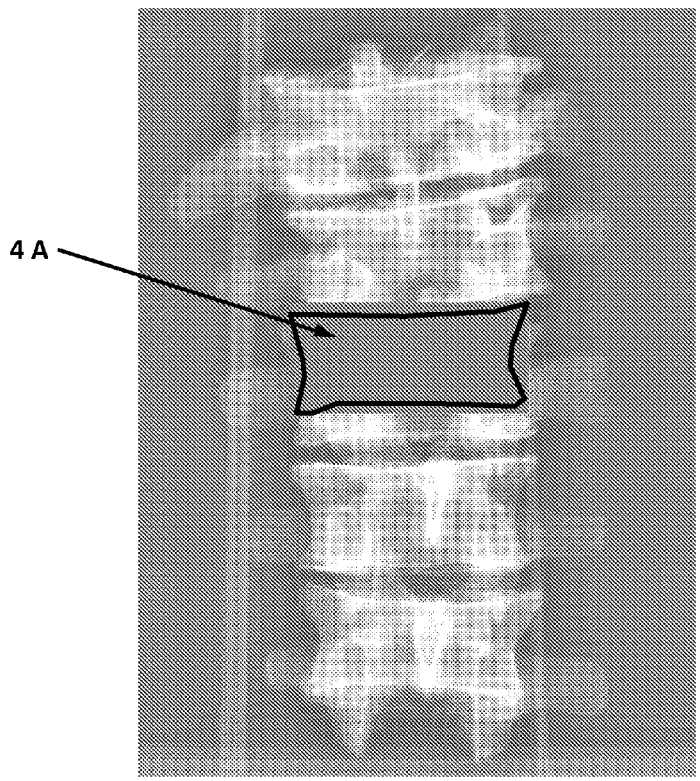
FIG. 4 is an X-ray image of a patient's spine showing a drawn region of interest where an implant will be placed.

Using a set of bone samples, for example spine samples, plain X-ray images of the spines are taken (FIG. 4), using standard imaging protocols. For each resulting image, one or several regions of interest 4A are drawn over the bone where the implant is to be placed. Then the texture analysis are performed, preferably using the above mentioned method described in U.S. Pat. No. 7,609,867. For each region of interest, the bone structural parameter is computed using several configurations $C_i$.

Using the same set of bone samples, the spine implants are placed in the previously defined locations. The implants' stability is then measured by measuring the force needed to pull out the implants from the bone samples. For each region of interest and each configuration of the texture analysis, the correlation between the pull-out force and the bone structural parameter is determined.

Last, the maximum of the correlation is determined and the corresponding configuration of the texture analysis is stored. This configuration $C_a$ is specific for the evaluation of the primary stability of this type of spine implants using this type of medical imaging device.

Using a plain X-ray image of a patient's spine where an implant is planned, a region of interest 4A is drawn on the bone image where the implant is to be placed. The texture analysis is computed using the configuration $C_a$. The resulting value allows to predict whether the planned implant will be stable immediately after placement (primary stability).

The invention claimed is:

1. A method of determining, prior to implanting a planned bone implant into a bone, an indicator of the stability of the planned bone implant after it has been implanted, the method comprising the steps of:
   Providing a two- or three-dimensional image, excluding distorted panoramic images, of a bone at a location where a bone implant is planned;
   Determining a bone structural parameter at said location from the two- or three-dimensional image, wherein the bone structural parameter is determined by a texture analysis of a two- or three-dimensional grey scale image in a region of interest at said location where the bone implant is planned, said texture analysis being performed directly on grey scale levels contained in the two- or three-dimensional image;
   Providing implant stability data which is related to data representing the bone structural parameter, wherein evaluation of said implant stability data comprises at least one of: Resonance Frequency Analysis of a reference implant; assessing the damping capacity of a reference implant; and biomechanical testing including measuring the pull-out strength of a reference implant; and
   Determining, from the determined bone structural parameter and from said implant stability data, an indicator for the stability of the planned bone implant after implantation at said location, comprising determining said indicator of the stability of the planned bone implant as a primary stability, which is the predicted stability of the implant at the day of implanting the implant into the bone.

2. The method of claim 1, wherein said bone implant is selected from the group consisting of a dental implant or an orthopaedic implant.

3. The method of claim 1, wherein said bone implant comprises a biomaterial, such as a bone substitute.

4. The method of claim 1, wherein said bone implant comprises a screw of inert material in particular of titanium.

5. The method of claim 1, further comprising determining said indicator of the stability of a planned bone implant after it has been implanted as a secondary stability, which is the predicted stability of the implant during and after healing and/or during and after osseointegration of the implant.

6. The method of claim 1, wherein a three-dimensional image is provided of the bone at the location where a bone implant is planned, and wherein the three-dimensional image is either projected onto a plane to be processed as a two-dimensional image or is processed as a three-dimensional image for determining the bone structural parameter.

7. The method of claim 1, wherein evaluation of said implant stability data comprises a histological analysis of the implants' osseointegration.

8. The method of claim 1, wherein the bone structural parameter is evaluated prior to implant as a predictor of the implant stability and after surgery to monitor the implant integration.

9. The method of claim 1, wherein the bone structural parameter is representative of trabecular bone texture.

10. The method of claim 1, wherein the bone structural parameter is determined by a series of the following steps a) to f) performed by a computational device configured to process a digitized two- or three-dimensional image:
   a) retrieving a grey level h(O) for each pixel in a region of interest of the two- or three-dimensional image;
   b) selecting a representative set of pixels at a distance r around h(O);

c) retrieving the grey level h(r) of said set of pixels;
d) computing a variance V(r) of the grey levels with the formula:

$$V(r)=[h(r)-h(O)]^2;$$

e) tracing a curve associated with V(r) on a log-log scale; and
f) determining the slope of the curve as said bone structural parameter.

* * * * *